(12) United States Patent
Kast et al.

(10) Patent No.: US 6,895,276 B2
(45) Date of Patent: May 17, 2005

(54) IN-LINE LEAD HEADER FOR AN IMPLANTABLE MEDICAL DEVICE

(75) Inventors: John E. Kast, Hugo, MN (US); Andrew J. Ries, Lino Lakes, MN (US); Kelly Grimes, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 351 days.

(21) Appl. No.: 10/090,045

(22) Filed: Feb. 28, 2002

(65) Prior Publication Data

US 2003/0163171 A1 Aug. 28, 2003

(51) Int. Cl.$^7$ .............................................. A61N 1/375
(52) U.S. Cl. ...................................... 607/37; 439/909
(58) Field of Search ........................... 607/37, 36, 38; 439/909

(56) References Cited

U.S. PATENT DOCUMENTS

| | | | |
|---|---|---|---|
| 4,226,244 A | 10/1980 | Coury et al. ............ 128/419 P |
| 4,469,104 A | 9/1984 | Peers-Trevarton ...... 128/419 P |
| 4,898,173 A | 2/1990 | Daglow et al. | |
| 4,934,366 A | 6/1990 | Truex et al. | |
| 4,934,367 A | 6/1990 | Daglow et al. ............. 439/527 |
| 4,971,057 A | 11/1990 | Theres .................... 128/419 P |
| 5,012,807 A | * 5/1991 | Stutz, Jr. ...................... 607/37 |
| 5,070,605 A | 12/1991 | Daglow et al. ............... 29/842 |
| 5,076,270 A | 12/1991 | Stutz, Jr. ................. 128/419 P |
| 5,304,219 A | 4/1994 | Chernoff et al. ............ 607/122 |
| 5,324,311 A | * 6/1994 | Acken .......................... 607/37 |
| 5,336,246 A | 8/1994 | Dantanarayana ............. 607/37 |
| 5,374,279 A | * 12/1994 | Duffin et al. ................... 607/5 |
| 5,431,695 A | 7/1995 | Wiklund et al. .............. 607/36 |
| 5,514,172 A | 5/1996 | Mueller ....................... 607/122 |
| 5,766,042 A | 6/1998 | Ries et al. .................... 439/668 |
| 5,795,165 A | 8/1998 | Jarl ............................. 439/86 |
| 5,843,141 A | 12/1998 | Bischoff et al. .............. 607/37 |
| 5,968,082 A | 10/1999 | Heil ............................. 607/37 |
| 6,198,169 B1 | 3/2001 | Kobayashi et al. ......... 257/780 |
| 6,321,126 B1 | 11/2001 | Kuzma ........................ 607/137 |
| 6,327,502 B1 | 12/2001 | Johansson et al. ............ 607/36 |

FOREIGN PATENT DOCUMENTS

| | | | |
|---|---|---|---|
| EP | 0 339 877 A2 | 11/1989 | .......... A61N/1/375 |
| WO | WO 00/64535 | 11/2000 | .......... A61N/1/375 |

* cited by examiner

*Primary Examiner*—Kennedy Schaetzle
(74) *Attorney, Agent, or Firm*—Girma Wolde-Michael

(57) ABSTRACT

Implantable medical devices (IMDs) comprising a monitor or implantable pulse generator (IPG) having an IPG header to which lead connector assemblies of electrical medical leads are coupled, particularly, an improved in-line IPG header providing enhanced durability, ease of manufacture, and ease of use. A stack of alternating, substantially tubular electrically insulating fluid seals and header connector elements is assembled in axial alignment to form a common, elongated axial stack bore sized in diameter and length to receive the lead connector assembly. Each adjacent electrical connector element and fluid seal are interlocked with one another during assembly of the stack to maintain the axial alignment and the length and diameter dimensions. Fluid seals are located at each end of the stack, and the stack can be inserted as a unit into a cavity of the IPG header.

19 Claims, 7 Drawing Sheets

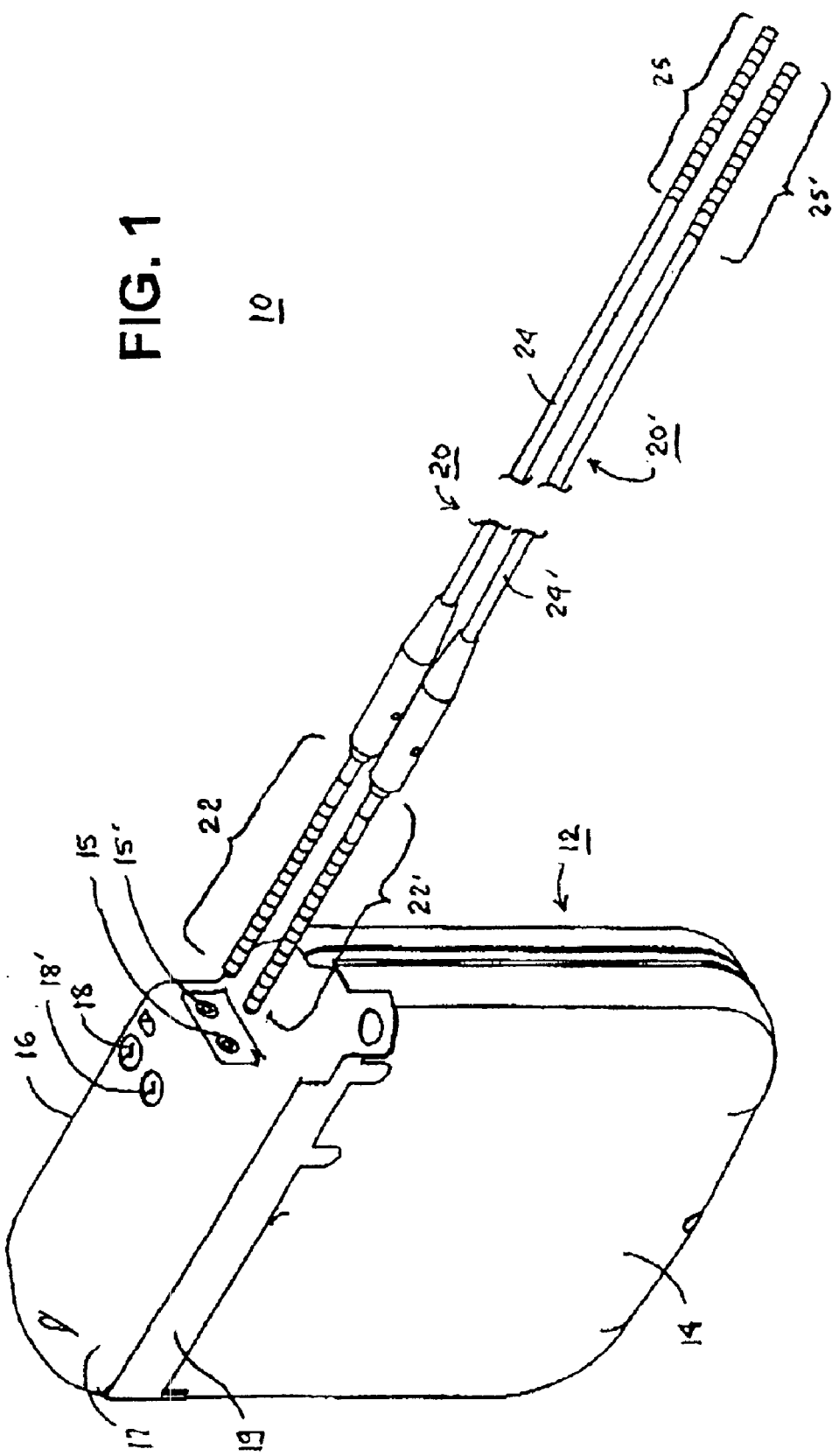

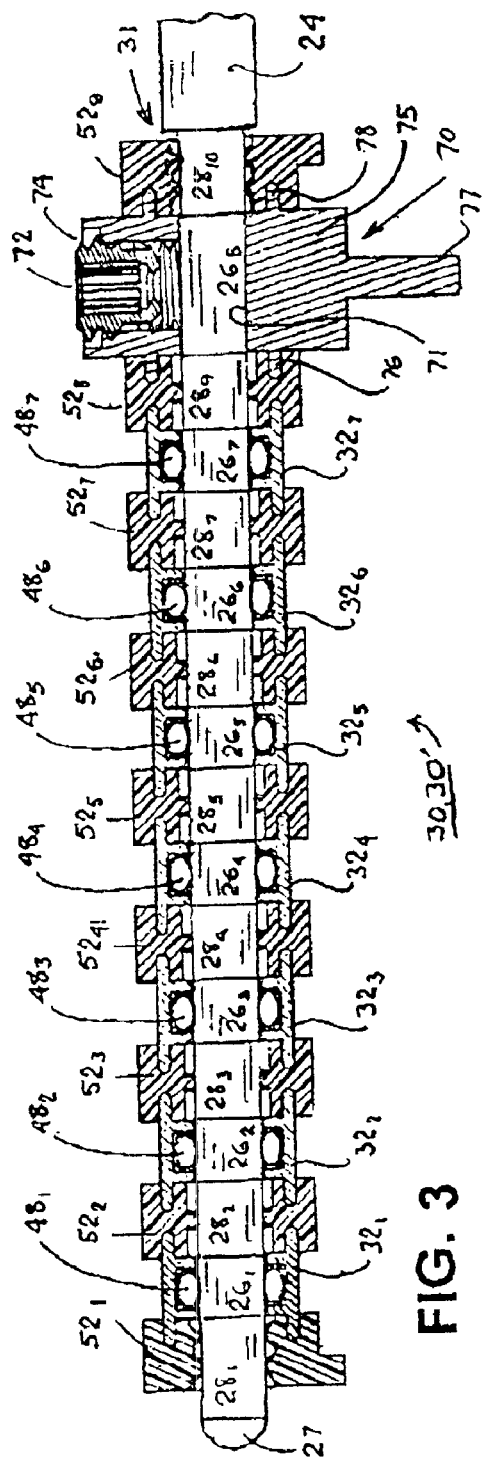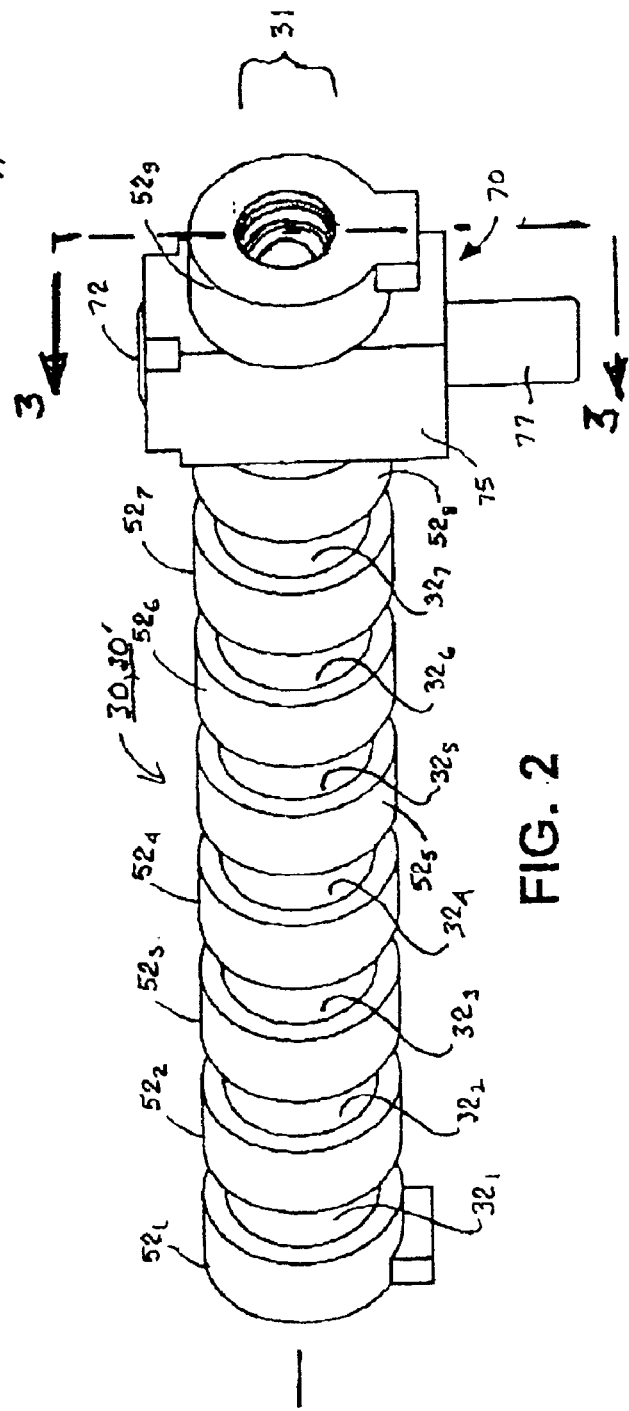
FIG. 3
FIG. 2

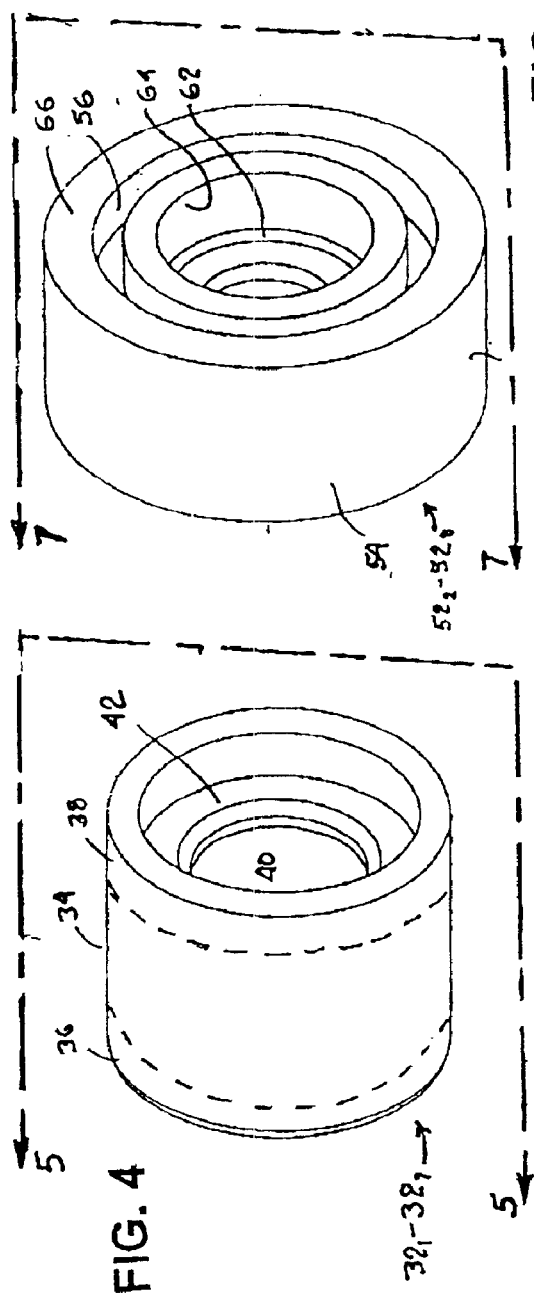
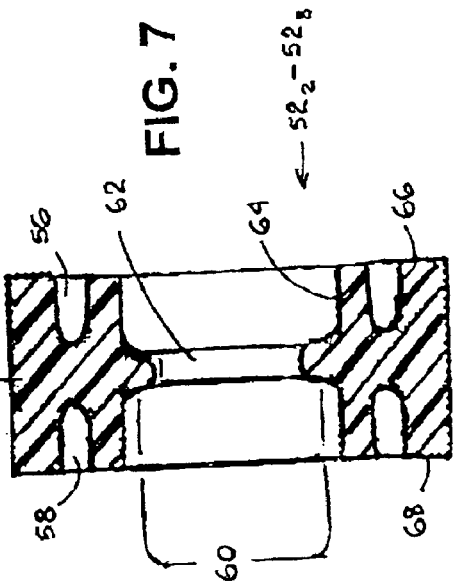
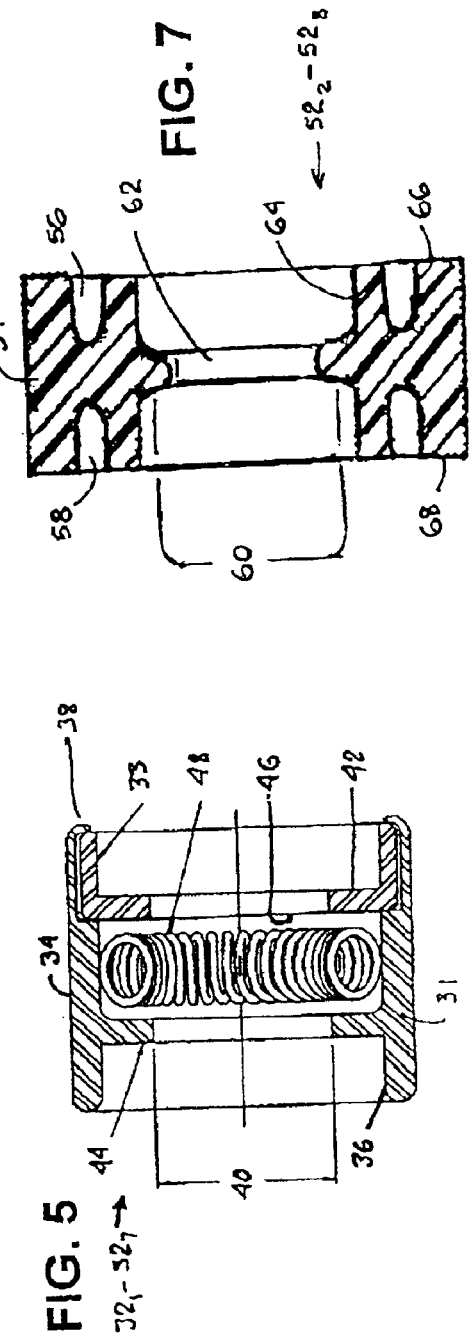

IN-LINE LEAD HEADER FOR AN IMPLANTABLE MEDICAL DEVICE

FIELD OF THE INVENTION

This invention relates generally to implantable medical devices (IMDs) comprising a monitor or implantable pulse generator (IPG) having an IPG header to which lead connector assemblies of electrical medical leads are coupled, and particularly, to improved in-line lead IPG headers providing enhanced durability, ease of use, and ease of manufacture.

BACKGROUND OF THE INVENTION

A wide variety of IMDs that employ electronic circuitry for providing electrical stimulation of body tissue and/or monitoring a physiologic condition are known in the art. A number of IMDs of various types are known in the art for delivering electrical stimulation therapies to selected body tissue and typically comprise an IPG for generating stimulating therapies and at least one electrical medical lead bearing a stimulation electrode for delivering the stimulating pulses to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. A wide variety of tissue stimulating IMDs are known for stimulating various nerves, the brain, the GI tract, the cochlea, and various muscles and organs for treating a variety of conditions. Further drug delivery IMDs have been developed to deliver drugs from a reservoir to body organs or structures through drug delivery catheters.

There are at least four paramount considerations or goals that are taken into account in the design and fabrication of such IMDs. First, the IMD operation must be safe, reliable and effective in delivering a therapy and/or monitoring a physiologic condition. Second, the IMD must be long lived and be cost-effective relative to alternative therapies. Third, the IMD must be reasonably miniaturized so that it can be implanted without being uncomfortable and cosmetically distressing to the patient. Finally, each new generation of IMD must satisfy the first three considerations while provide an ever increasing number of performance features and functions that are clinically beneficial to the patient and useful to the medical community.

Electrical medical leads typically comprise a lead body extending between lead proximal and distal ends and comprising one or more electrical conductors and in many cases a lead body lumen extending between the lead proximal and distal ends. One or more electrode and/or sensor are located along the lead body, typically at or near the lead distal end, and are electrically connected to a lead conductor. A lead connector element for each lead conductor is located in a lead connector assembly at the lead body proximal end and is adapted to be coupled to an electrical terminal of the monitor or IPG.

Unipolar, bipolar and multi-polar electrical medical leads have been developed having one, two and three or more, respectively, lead conductors, electrodes/sensor terminals and lead connector elements. Typically, lead connector elements comprise at least a proximal connector pin in unipolar leads and additional, more distally located connector rings in bipolar and multi-polar electrical medical leads that are arrayed in-line, separated by insulator bands, along the length of the lead connector assembly. A proximal lumen end opening is provided in the connector pin of medical electrical leads having lead lumens extending to or through the lead end. Industry wide international standards have been adopted that dictated the diameter and length dimensions and spacing of the connector pin and ring(s). In one typical case, the connector pin has a diameter that is smaller than the connector ring(s), and the connector pin and rings are separated by insulators having outwardly extending sealing rings providing fluid seals comporting with the IS-1 standard.

Implantable monitors and IPGs, as well as implantable drug dispensers, generally have taken the form of a hermetically sealed IMD housing, enclosing a power source and electronic circuitry (and a drug delivery reservoir in the case of drug delivery IMDs), and a connector header or block. For convenience and not by way of limitation, the two parts of all such IMDs that are joined together in use are referred to herein as: (1) an IPG comprising an IPG housing and an IPG connector header; and (2) an electrical medical lead. Electrical feedthroughs extending through the IPG housing couple the electronic circuitry with one or more IPG header connector elements that electrically and mechanically engage the lead connector elements. The electronic circuitry provides stimulation therapies through the electrodes and/or processes signals picked up through the lead-borne electrodes and/or sensors.

The lead connector assembly must be joined with the IPG header in a manner that assures the safety and reliability of the IMD over its lifetime. At present, most IPG headers are formed from biocompatible plastic having one or more elongated bore shaped to snugly receive a lead connector assembly and to establish electrical and mechanical contact between the lead connector elements and respective IPG header connector elements. The bore of the header typically contains one or more annular connector element that engages with a respective one of the connector pin and connector ring(s) located of the proximal lead connector assembly. The engagement has been historically accomplished by tightening a setscrew transverse to the bore of the IPG header connector element so that the setscrew tip securely abuts the lead connector pin or ring extending through the connector element bore as disclosed in commonly assigned U.S. Pat. No. 4,226,244.

The IPG header bore and mating lead connector assembly satisfy an aforementioned international connector standard, e.g., the IS-1 connector standard commonly in use in conjunction with implantable pacemakers and defibrillators, corresponding generally to the connector configurations illustrated in U.S. Pat. Nos. 5,076,270, 5,514,172, and 5,431,695. Various atypical connector assemblies and assembly standards have been proposed, most significantly, dictating common diameters, lengths and spacing between all lead connector elements without any insulating rings extending outward from the insulators, e.g. the mating lead and IPG connector configuration depicted in commonly assigned U.S. Pat. Nos. 5,070,605 and 5,843,141. Numerous other proposals for such multi-polar in-line connector systems have been put forward, as set forth in U.S. Pat. Nos. 4,934,367, 5,304,219, 4,971,057, 6,327,502, and 4,469,104.

The connection standards continue to evolve in order to accommodate an increasing number of electrical connections between lead connector elements and the IMD circuitry within the IPG housing, while maintaining the integrity of the electrical and mechanical connections, providing a seal against ingress of body fluids, simplifying the connection steps, minimizing overall size of the IPG header, and accomplishing all of these goals economically. The number of connections required is increasing in the field of cardioversion/defibrillation and cardiac pacing in order to accommodate upper and lower and right and left heart chamber pacing and cardioversion/defibrillation. There is a long recognized need to be able to provide timed neurological stimulation to four or more separated sites of the spinal cord or nerves to alleviate pain or muscle groups to achieve functional electrical stimulation or the brain to alleviate tremors and the like. In the field of cochlear implants, there is a need to be able to make up to 32 connections as indicated in U.S. Pat. Nos. 6,321,126 and 6,198,169. However, new connector designs are advanced in the '126 and '169 patents that avoid using the widely accepted in-line connector configuration comprising an in-line lead connector assembly and IPG header bore as described above.

Generally, it is desirable to minimize the cross-section of the header bore and the corresponding diameter of the lead connector assembly, space the respective connector elements close together and reduce the minimize the size of the connection and attachment parts. The use of a setscrew to attach each respective lead and IPG connector element together limits the ability reduce overall size. A tripolar, in-line connector configuration and a quadripolar, in-line connector configuration are depicted in commonly assigned U.S. Pat. No. 5,766,042 and in the above-referenced '141 patent, respectively, that seek to maximize the number of connections that can be accomplished in the space allotted to the header without using setscrews. Many component changes have been proposed to eliminate the use of setscrews in favor of header connector elements that are spring-loaded or otherwise act to firmly grip the lead connector elements with friction and compression as the connector assembly is inserted into the IPG header bore as disclosed, for example, in the above-referenced '605 patent and in U.S. Pat. Nos. 5,795,165 and 5,968,082. Cam mechanisms to lock the lead connector assembly into the header bore are also disclosed in the above-referenced '042 and '297 patents, for example.

The above-referenced '141 patent discloses a practical, multi-polar, in-line IPG header and lead connector assembly configuration and a connector system for use in interconnecting the same. Typically, lead connector assemblies are pushed into the header bore until the lead pin is fully seated in the deepest part of the bore and the pin end abuts the bore end. But, the header bore of the '141 patent is open ended such that the lead connector assembly can be pulled through the header bore by a tool extending all the way through the bore and fitted into the lead lumen. Although a setscrew is not shown in the depicted embodiments, a single setscrew could be provided to secure the lead connector assembly once it is pulled through the header bore as suggested in the '141 patent.

The IPG header embodiments disclosed in the '141 patent are formed of a rigid header base having an elongated bore extending through it that is shaped with four aligned recesses that each receive a miniature tubular connector element and insulating fluid seal arranged end-to-end so that they are axially aligned. Each recess is sized so that each set of header connector elements and insulating fluid seals abut one another and bulkheads separating the recesses in order to remain in place under axial load. The lumens of the four sets of connector elements and insulating fluid seals are aligned axially to form the header bore receiving the lead connector assembly. The lumens of the tubular header connector elements are formed with spring elements to frictionally engage the lead connector rings, and the lumens of the tubular fluid seals are formed with inward directed annular sealing rings to engage insulating rings of the lead connector assembly. The metal tubular connector elements are axially rigid, but the elastomeric, electrically insulating, fluid seals are compressible axially and diametrically.

During fabrication, the four sets of header connector elements and insulating fluid seals are inserted into a cavity of the header base such that the bores of the header connector elements and insulating fluid seals are aligned axially to define the header bore when assembly is completed. Electrical conductors extending from the housing supported electrical feedthrough pins are bent over and welded to the exterior surfaces of the tubular connector elements. Elastomeric silicon rubber of epoxy or the like is injected into the base bore to surround and insulate the exposed surfaces of the four sets of header connector elements and insulating fluid seals and the conductors.

While a high degree of miniaturization of the IPG header is achieved, the embodiments disclosed in the '141 patent have proven difficult to assemble and use.

A further in-line implantable medical lead connection system for connecting in-line lead connector assemblies with either IPG headers or lead extension is disclosed in PCT Publication No. WO 00/64535. The IPG header or lead extension connector is formed of a setscrew connector element and a plurality of miniature tubular connector elements and insulating fluid seals arranged end-to-end so that they are axially aligned to form the header bore. Each tubular connector element is formed having an interior channel that traps a continuous coil spring that is wound on an angle that defines and surrounds the connector element bore and that is compressed when contacted by a lead connector element inserted through the connector element bore. Presumably, the elements of the array, as well as a strain relief element, are lined up and held in alignment, perhaps by a mandrel inserted through the aligned bores or an external cage or the like, while the insulative housing of the lead extension or IPG header is molded about the array. Similar uses of trapped continuous coil, IPG connector elements are disclosed in U.S. Pat. Nos. 5,076,270 and 5,336,246.

There remains a need for a miniaturized in-line connector system for IMDs that is simple and inexpensive to fabricate and is reliable in use.

SUMMARY OF THE INVENTION

The present invention is directed toward providing a practical, multi-polar in-line connector system for use in interconnecting implanted stimulators and associated leads which may workably be employed in conjunction with lead connector assemblies having three, four or more lead connector elements located in-line along a single, non-bifurcated connector assembly inserted within a single header bore of an IPG header. In addition, the invention is directed toward providing such a connector system in a fashion that allows the use of tool-less, frictional, compressive electrical connections of the sort described above for most or all of the electrical interconnections. Optionally, at least one setscrew connector element can be included in the practice of the invention, wherein the setscrew can be tightened against a feature of the lead connector assembly to inhibit retraction of the lead connector assembly from the header bore.

In accordance with one aspect of the present invention, a stack of alternating, tubular electrically insulating fluid seals and header connector elements is assembled in axial alignment, the stack having a stack length between stack proximal and distal ends. In this way, fluid seals separate the IPG header connector elements from one another, and the stack provides a common, elongated axial stack bore sized in diameter and length to receive the lead connector assembly. Each adjacent electrical connector element and fluid seal are interlocked with one another during assembly of the stack to maintain the axial alignment and the length and diameter dimensions. Each electrical connector element and fluid seal has a predetermined axial length between annular ends thereof, and the combined axial lengths of the total number of electrical connector elements and fluid seals define the stack length. Fluid seals are located at each end of the stack, and the stack can be inserted as a unit into a cavity of the IPG header.

Each electrical connector element is formed with an annular U-shaped interior channel defined between connector element annular end walls into which a connector spring element is fitted. The spring element can comprise a continuous coil spring of the types disclosed in the above-referenced '270 and '246 patents and WO 00/64535 publication that is retained or trapped in the channel and that intrudes slightly into the stack bore whereby the spring element is compressed by a lead connector element inserted into the stack bore. The fluid seal is formed with one or more annular sealing ring formed in the seal lumen having a smaller diameter than the seal lumen so that the sealing ring intrudes slightly into the stack bore whereby the sealing ring is compressed by a lead insulator inserted into the stack bore. In this way, secure, frictional electrical and mechanical contact is made between lead connector elements and the header connector elements, and the sealing rings seal the electrical connections from fluid ingress.

In one embodiment, the tubular fluid seals and connector elements are interlocked by mating annular male flanges and female grooves that are sized to be fitted together, so that the stack can be assembled together. The annular male flanges extend from or form the annular ends of the connector elements, and the annular female grooves are recessed into the annular ends of the tubular fluid seals. The annular male flanges and annular female grooves are sized in width to provide interference frictional fit in an annular, tongue-in-groove manner. Annular female grooves are not formed in the annular ends of the tubular fluid seals located at the stack ends. Alternatively, a stiffening ring is inserted into the annular female grooves in the annular ends of the tubular fluid seals located at the stack ends.

In a second embodiment, the tubular connector elements are formed in two parts that are fitted together. The first part comprises one of the connector element end walls that define the U-shaped channel when the parts are fitted together. This embodiment facilitates insertion of the continuous coil spring into the U-shaped channel.

In both embodiments, the stack can further comprise a setscrew connector element preferably located at one end of the stack. The setscrew connector element has a connector element bore that is axially aligned with and part of the stack bore and a setscrew bore that is transverse to the connector element bore and contains a setscrew adapted to be tightened against a segment of the lead connector assembly within the connector element bore. The setscrew connector element is formed with annular male flanges extending from or forming the annular ends of the setscrew connector elements that are fitted into annular female grooves of the tubular fluid seals bracketing the setscrew connector element.

In fabrication of an IPG header, the stack is assembled from N tubular unitary or two-part, spring-loaded, connector elements and N+1 tubular fluid seals, or N tubular unitary or two-part, spring-loaded, connector elements, one setscrew connector element and N+3 tubular fluid seals. The stack is fitted into a recess of an IPG header base. In IPG headers designed to have two header bores, two such stacks are inserted side-by-side into respective side-by-side recesses in the IPG header base. Electrical conductors, e.g., an array of preformed Niobium ribbons, are inserted into slots of the base and their free ends are welded to the tubular connector elements of the stack. The exposed stack(s) is over-molded with an elastomeric compound to fill the remaining space of the recess or recesses and present a finished outer surface. Optionally, a header cover formed of the same material as the header base can then be fitted over and adhered to the over-molded assembly, e.g., by ultrasonic welding of the edges of the cover to the base.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other features and advantages of the invention will become apparent to those skilled in the art from the following detailed description of a preferred embodiment, especially when considered in conjunction with the accompanying drawings in which:

FIG. 1 is a schematic an IMD comprising a pair of implantable medical leads and an IPG formed of an IPG housing and an IPG header in accordance with a first embodiment of the invention;

FIG. 2 is an expanded perspective view of an IPG connector stack incorporated into the IPG header of FIG. 1;

FIG. 3 is a partial cross-section view of the IPG header taken along lines 2—2 of FIG. 2 illustrating the lead connector assembly inserted into the bore of the stack of first embodiment of the present invention;

FIG. 4 is an expanded perspective view of a tubular connector element of the stack of FIG. 2;

FIG. 5 is a cross-section view taken along lines 5—5 of FIG. 4 illustrating the connector element bore, channel, and garter spring retained therein of the tubular connector element;

FIG. 6 is an expanded perspective view of a tubular fluid seal of the stack;

FIG. 7 is a cross-section view taken along lines 7—7 of FIG. 6 illustrating the seal bore;

DETAILED DESCRIPTION OF THE PREFERRED EMBODIMENTS OF THE INVENTION

Figure 8:
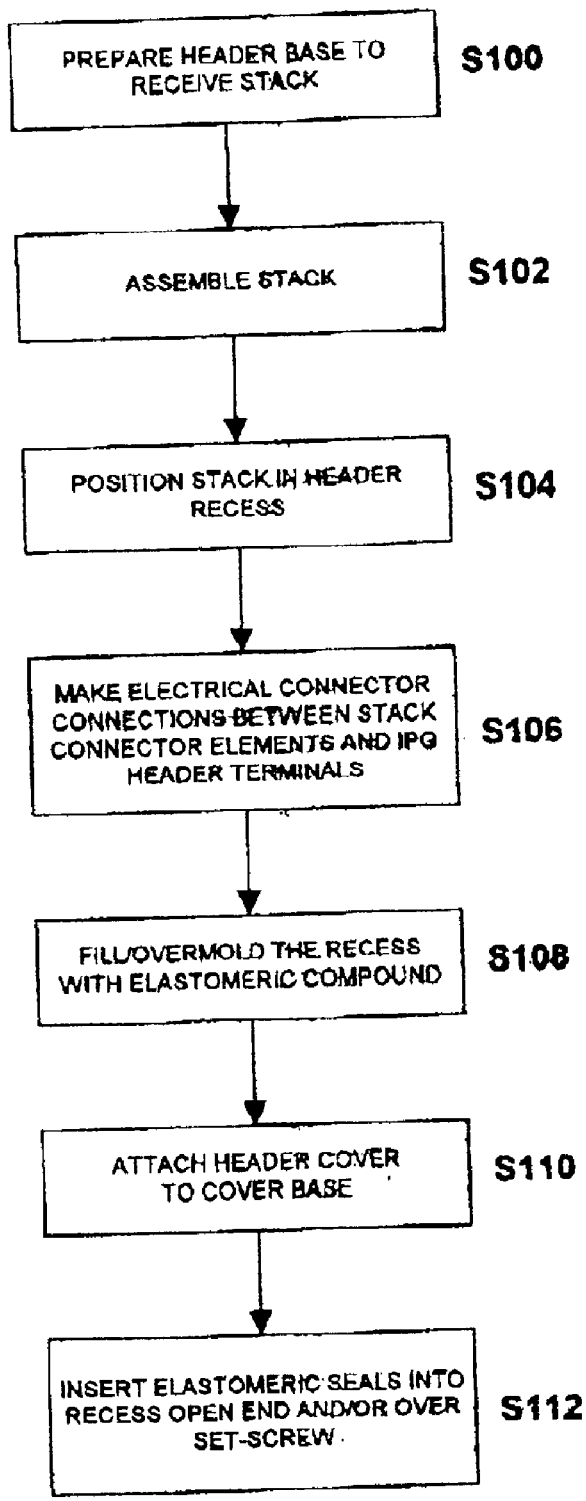
FIG. 8 is a flow chart of the assembly process for assembling an IPG header view of a header base.
Figure 9:
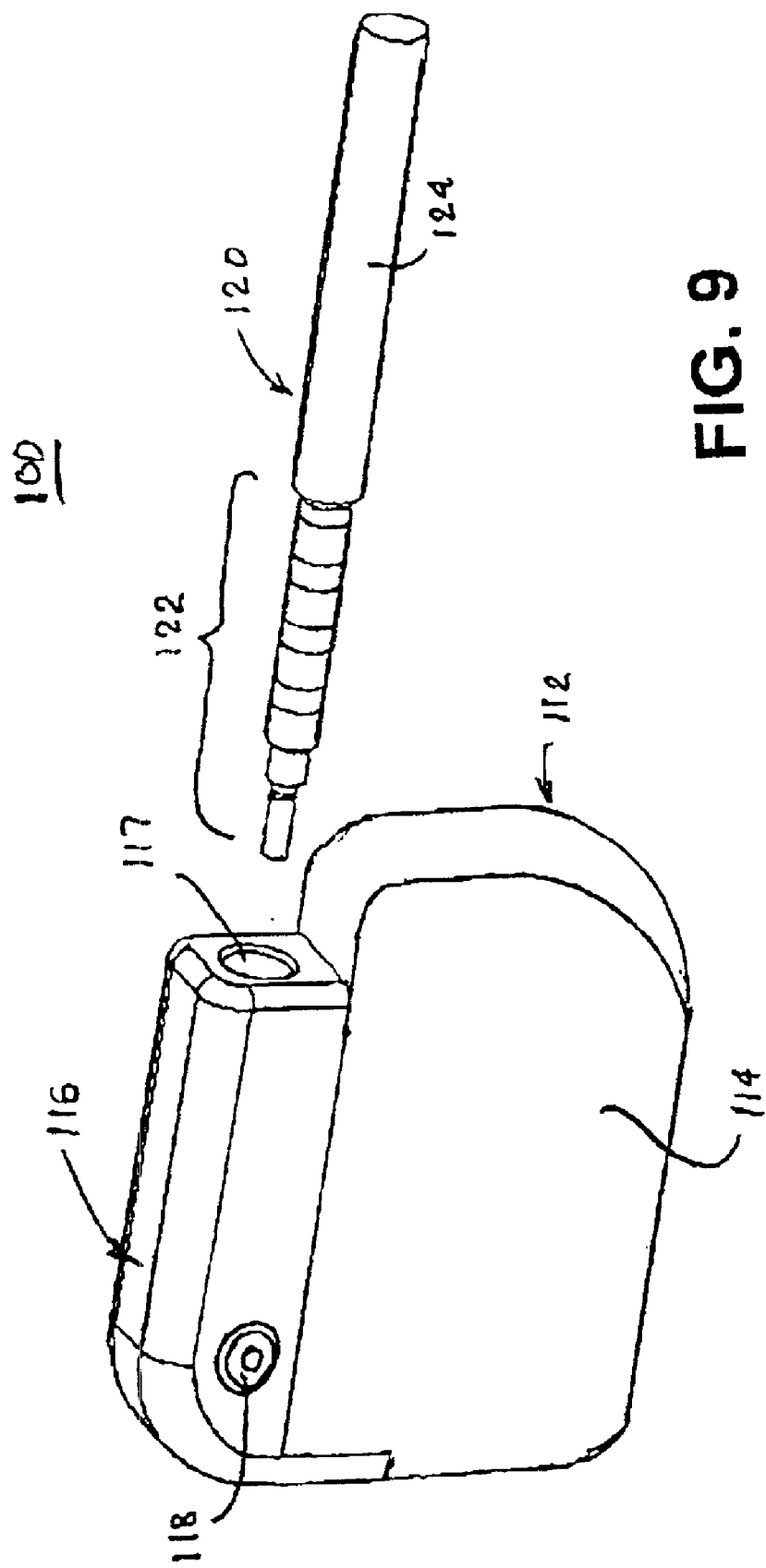
FIG. 9 is a schematic an IMD comprising an implantable medical lead and an IPG formed of an IPG housing and an IPG header of a second embodiment of the invention.
Figure 10:
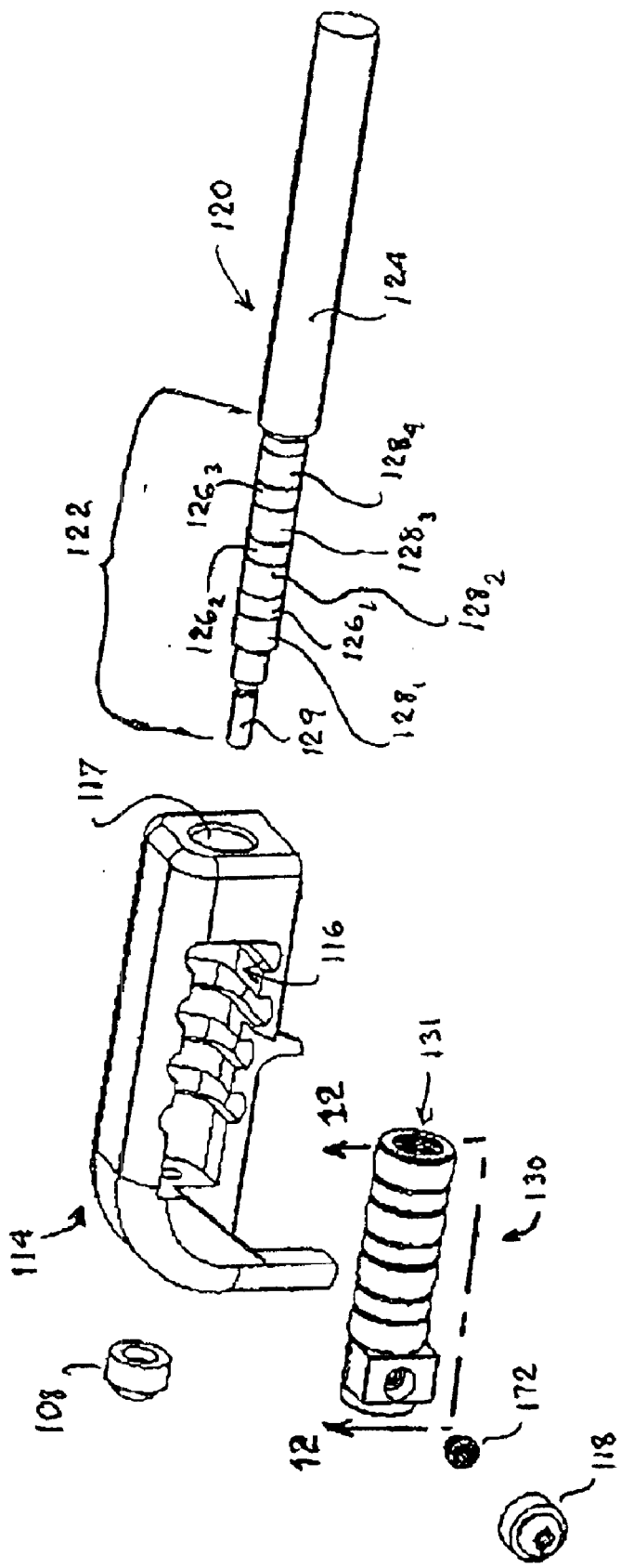
FIG. 10 is an exploded view of IPG header of FIG. 9 illustrating the stack and associated components of the IPG header of FIG. 9.

The present invention can be implemented in a wide variety of IMDs currently existing or that may come into existence that require the attachment of connector elements an elongated medical lead or other elongated medical instrument with a further part of the medical device. For convenience and not by way of limitation, the present invention is described in the context IMDs 10, 100 comprising: (1) an IPG 12 comprising an IPG housing 14, 114 and IPG header or header 16, 116; and (2) an electrical medical lead 20, 20', 120. Electrical feedthroughs extending through the IPG housing 14, 114 couple the electronic circuitry with one or more IPG header connector elements that electrically and mechanically engage the lead connector elements. The electronic circuitry provides stimulation therapies through the electrodes (not shown in the figures) and/or processes signals picked up through the lead-borne electrodes and/or sensors (not shown in the figures). Thus, the term "IPG" in the specification and claims embraces both pulse generators and monitors.

A first specific embodiment of the invention is described herein in reference to FIG. 1 through FIG. 8 that enables the attachment of two multi-polar electrical medical leads 20, 20' to the IPG header 16 of IPG 12. The IMD 10 of the first embodiment can constitute a neurostimulator for generating and delivering neurostimulation pulse trains to a plurality of electrodes in linear electrode arrays 25, 25' arrayed in therapeutic relation to body organs, muscles or nerves or a multi-chamber cardiac pacing system or the like.

The leads 20, 20' shown in FIGS. 1 and 2 are depicted inserted into a header bores 15, 15' of the IPG header 16. The leads 20, 20' comprise elongated lead bodies 24, 24' that encloses a plurality of conductors (not shown), in this case eight conductors. The eight electrical conductors are electrically connected to eight respective lead connector elements $26_1$–$26_8$ (enumerated in FIG. 3) that are each arranged in lead connector element arrays or lead connector assemblies 22, 22' along a proximal segment of the lead bodies 24, 24' and to the eight electrodes in the distal electrode arrays 25, 25'. The lead connector elements $26_1$–$26_8$ are separated from one another and from the proximal lead tip 27 and by a plurality of lead insulator elements or insulation sleeves $28_1$–$28_{10}$ as shown in FIG. 3. The leads 20, 20' can take the form of any electrical medical lead using conventional materials for the lead connector elements $26_1$–$26_8$ and the plurality of insulation sleeves $28_1$–$28_{10}$ and any form of lead conductors, electrodes and/or sensors supported by the lead body 24, and such particulars of the lead construction and function are not important to the present invention.

The IPG header 16 is formed as described in detail herein from a preformed header base 19, a preformed header cover 17, and a pair of penetrable setscrew seals 18 and 18'. The header cover 17 and header base enclose a pair of elongated stacks 30, 30' shown in FIGS. 2 and 3 having stack bores that are axially aligned with and constitute the IPG header bores 15 and 15' into which the lead connector assemblies 22, 22' are inserted.

The stacks 30 and 30' each comprise seven header connector elements $32_1$–$32_7$ and a setscrew connector element 70 that are each separated from the next by tubular, elastomeric, electrically insulating, fluid seals $52_1$–$52_9$. The seven header connector elements $32_1$–$32_7$, the setscrew connector element 70 and the nine tubular, elastomeric, electrically insulating, fluid seals $52_1$–$52_9$ are assembled in axial alignment, so that the stack 30, 30' extends through a stack length between stack proximal and distal ends. The connector elements $32_1$–$32_7$ and setscrew connector element 70 are separated from one another by fluid seals $52_1$–$52_9$, and the stack 30, 30' provides a common, elongated axial stack bore 31 sized in diameter and length to receive the lead connector assembly 22.

Each fluid seal $52_1$–$52_9$ is interlocked with an adjacent electrical connector element $32_1$–$32_7$ or the setscrew connector element 70 during assembly of the stack 30, 30' to electrically isolate the electrical connector element $32_1$–$32_7$ and the setscrew connector element 70 and to maintain the axial alignment and the length and diameter dimensions. Each electrical connector element $32_1$–$32_7$ and fluid seal $52_1$–$52_9$ has a predetermined axial length between annular ends thereof, and the combined axial lengths of the total number of electrical connector elements and fluid seals define the stack length. Fluid seals $52_1$ and $52_9$ located at each end of the stack 30, 30'.

Each individual electrical connector elements 32 is shown in greater detail in FIGS. 4 and 5. Each electrical connector element 32 is formed of an element housing 31 and a continuous coil spring 48. The element housing 31 can comprise a single part or two parts 33 and 35 shown in FIG. 5 that are fitted together to form an annular U-shaped interior channel 46 defined between connector element annular end walls 42 and 44 extending inward from the connector element cylindrical sidewall 34 and defining a connector element bore 40. The continuous coil spring 48 fitted into the channel 46 bore can comprise an annular garter spring or a slanted coil spring of the type provided by Bal Seal, Inc., located in Boulder. Colo. The coil spring 48 is retained or trapped in the channel 46 and that intrudes slightly into the connector element bore 40 which becomes part of the stack bore 31, whereby the coil spring 48 is compressed by a lead connector element inserted into the stack bore 31 as shown in FIG. 2. In this way, secure, frictional electrical and mechanical contact is made between lead connector elements $26_1$–$26_8$ and the header connector elements $32_1$–$32_7$.

One way of assembling the electrical connector element 32 is depicted in FIG. 5. The coil spring 48 is inserted against the annular end wall 44 of connector element part 31, and the annular end wall 46 of connector part 33 is fitted into an annular recess of connector element part 31. Nested annular flanges of the connector element parts 31 and 33 are attached together by staking and/or welding along the seam of the contacting annular surfaces. The attached nested annular flanges then become an annular male flange 38 of the electrical connector element 32 that extends away from annular end wall 46 in parallel alignment with the connector element axis and the stack axis. A further annular male flange 36 extends in the opposite direction away from the annular end wall 44 in parallel alignment with the connector element axis and the stack axis.

An individual fluid seal 52 among the fluid seals $52_2$–$52_8$ of FIGS. 2 and 3 is shown in greater detail in FIGS. 6 and 7. The fluid seal 52 is formed of a flexible elastomeric material, e.g. silicone rubber or soft polyurethane, and is generally tubular having a sidewall 54 extending between annular end walls 66 and 68 defining a fluid seal lumen or bore 60. One or more annular sealing ring 62 is formed extending inward in the seal bore 60 so that the sealing ring intrudes slightly into the stack bore 31, whereby the sealing ring 62 is compressed by a lead insulator inserted into the connector bore defined by the stack bore 31. In this way, the sealing rings 62 of the fluid seals $52_2$–$52_8$ seal against the insulation sleeves $28_2$–$28_9$ to seal the stack bore 31 and the electrical connections from fluid ingress.

Returning to stack 30, 30' depicted in FIGS. 2 and 3, it will be noted that the stack 30, 30' further comprises stack end fluid seals $52_1$ and $52_9$ that have two fluid sealing rings. Furthermore, fluid seal $52_1$ does not have an annular female groove 58 and fluid seal $52_9$ does not have an annular female groove 56. It should be noted that sealing rings 62 are not necessarily needed on all of the fluid seals $52_1$–$52_9$, but specifying sealing rings 62 on all of the fluid seals $52_1$–$52_9$ simplifies parts specification and assembly of the stack 30, 30'. Tabs extending from the stack end fluid seals $52_1$ and $52_9$ simplify identification of these seals $52_1$ and $52_9$ during assembly.

As noted above, the stack 30, 30' comprises a setscrew connector element 70 preferably located at one end of the stack 30, 30'. The setscrew connector element 70 comprises a setscrew connector block 75 and setscrew 72 fitted into a threaded bore 74. The connector block 75 is formed with a connector element bore 71 that is axially aligned with and part of the stack bore 31. The setscrew 72 and threaded bore 74 are transverse to the connector element bore 71, and the setscrew 72 is adapted to be tightened against a segment of the lead connector assembly 22 within the connector element bore 71. The setscrew connector block 75 can be used as an IPG connector element by electrical connection with the pin 77 so that the segment of the lead connector assembly 22 within the connector element bore 71 comprises a lead connector element $26_8$ as depicted in FIG. 3. The setscrew connector block 75 is formed with annular male flanges 76 and 78 extending in parallel alignment with the stack bore 31 that are fitted into annular female grooves of the tubular fluid seals $52_8$ and $52_9$ bracketing the setscrew connector element 70.

As shown in FIGS. 2 and 3, the tubular fluid seals $52_1$–$52_9$, the connector elements $32_1$–$32_7$ and the setscrew connector element 70 are interlocked by fitting each respective annular male flange 36, 38, 76, 78 into an annular female groove 56, 58 to assemble the stack 30, 30'. The annular male flanges 36, 38, 76, 78 and annular female grooves 56, 58 are sized in width to provide an interference frictional fit. The annular flanges 36, 38, 76, 78 fitted into an annular female groove 56, 58 stiffen the sidewalls 54 of each of the tubular fluid seals $52_1$–$52_9$ so that axially applied force during insertion or withdrawal of the lead connector assembly 22 into or out of the stack bore 31 does not unduly distort the fluid seals and sealing rings.

The method of assembling an IPG connector block incorporating the stack 30, 30' is depicted in FIG. 8. First a pre-molded header base 19 is prepared in step S100. The stacks 30 and 30' are assembled as described above in step S102. The stacks 30 and 30' are fitted into respective side-by-side cavities or recesses or a single enlarged cavity or recess of header base 19 in step S104. In IPG headers designed to have a single IPG header bore, only one such stack 30 is inserted into in the header base 19. Electrical conductors, e.g., an array of preformed Niobium ribbons, are inserted into slots of the header base 19 and their free ends are welded to the connector elements of the stacks 30, 30' in step S106. The exposed stacks 30, 30' are over-molded with an elastomeric compound, e.g., silicone rubber, to fill the remaining space of the recess or recesses and present a finished outer surface in step S108. The annular flanges 36, 38, 76, 78 fitted into an annular female groove 56, 58 also stiffen the sidewalls 54 of each of the tubular fluid seals $52_1$–$52_9$ so that externally applied pressure applied during sealing or molding of the stacks 30 and 30' into the cavity or recess or over-molding of the stacks 30 and 30' with the header base 19.

In this particular embodiment, a header cover 17 formed of the same material as the header base 19 is then fitted over and adhered to the over-molded assembly, e.g., by ultrasonic welding of the edges of the cover 17 to the base 19 in step S110. The cover 17 can be first fitted over the openings of the recesses and stacks 30, 30', and liquid polymer injected into the remaining space of the recess or recesses. Penetrable seals 18 and 18' are fitted into an opening of the header cover 17 and adhered thereto over the setscrew 72 that is penetrated by a hex wrench or other shaped tool to engage and rotate the setscrew 72 and reseals upon removal of the tool.

A second specific embodiment of the invention is described herein in reference to FIGS. 9–12 that enables the attachment of one or two multi-polar electrical medical leads 120 to the IPG header 116. The IMD 100 of the second embodiment can constitute an ICD or a cardiac pacemaker for generating and delivering cardioversion/defibrillation and/or pacing therapies to the heart. The lead 120 shown in FIGS. 1 and 2 is depicted inserted into a header bore 117 of the IPG header 116. The lead 120 comprises an elongated lead body 124 that encloses a plurality of conductors (not shown), in this case four conductors, that are electrically connected to four respective lead connector elements 129 and $126_1$–$126_3$ that are arranged in the lead connector element array 122 along a proximal segment of the lead body 124. Lead connector elements $126_1$–$126_3$ are conductive rings having a ring diameter, and lead connector element 129 is a pin having a pin diameter smaller than the ring diameter. The lead connector elements 129 and $126_1$–$126_3$ are separated from one another by a plurality of lead insulator elements or insulation sleeves $128_1$–$128_4$. The lead 120 can take the form of any electrical medical lead using conventional materials for the lead connector elements 129 and $126_1$–$126_3$ and the insulation sleeves $128_1$–$28_4$ and any form of lead conductors, electrodes and/or sensors supported by the lead body 124, and such particulars of the lead construction and function are not important to the present invention.

The IPG header 116 is formed as described in detail herein to enclose an elongated stack 130 comprising three header connector elements $132_1$–$132_{73}$ and a setscrew connector element 170 that are each separated from the next by tubular, elastomeric, electrically insulating, fluid seals $152_1$–$152_9$. The three header connector elements $132_1$–$132_3$, the setscrew connector element 170 and the four tubular, elastomeric, electrically insulating, fluid seals $152_1$–$152_4$ are assembled in axial alignment, so that the stack 130 extends through a stack length between stack proximal and distal ends. The connector elements $132_1$–$132_3$ and setscrew connector element 170 are separated from one another by fluid seals $152_1$–$152_4$, and the stack 130 provides a common, elongated axial stack bore 131 sized in diameter and length to receive the lead connector assembly 122.

Figure 11:
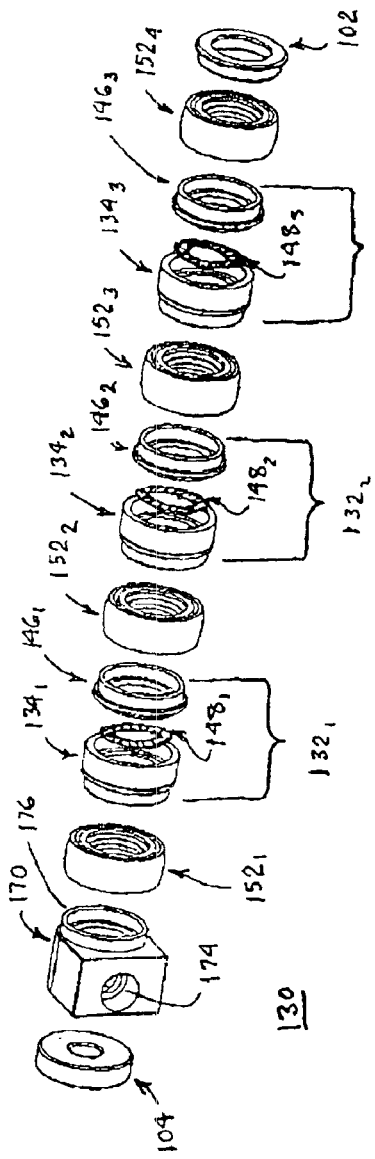
FIG. 11 is an exploded perspective view of the stack of FIG. 10.
Figure 12:
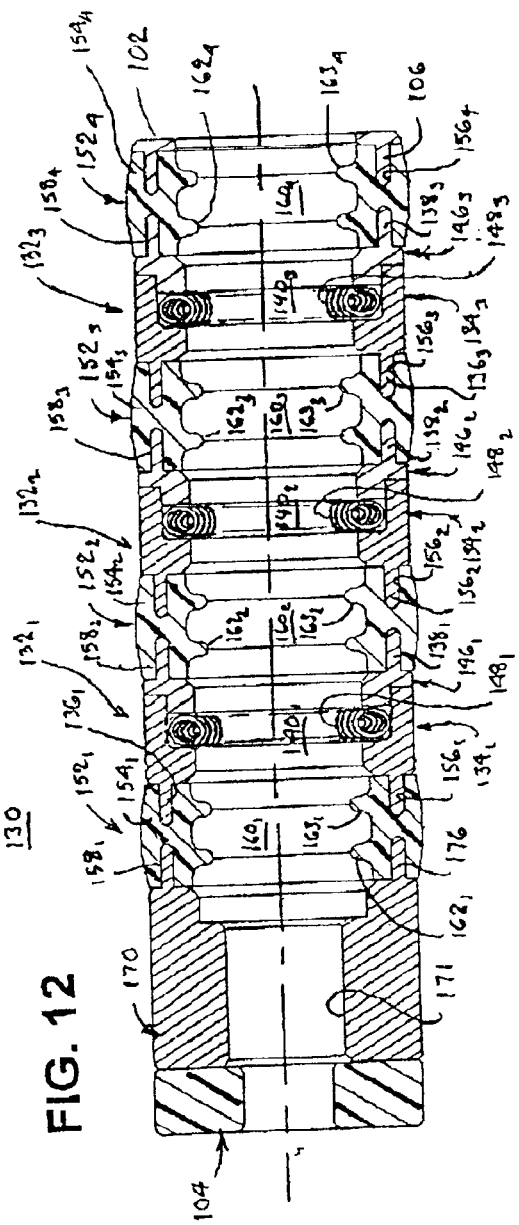
FIG. 12 is a cross-section view taken along lines 12—12 of FIG. 10 illustrating a two-part tubular connector element, a continuous spring fitting into the connector element channel, a tubular fluid seal, a setscrew connector element, and an end ring fitted into the end of an end fluid seal.

The stack 130 is shown in greater detail in FIGS. 11 and 12. Each fluid seal $152_1$–$152_4$ is interlocked with an adjacent electrical connector element $132_1$–$132_3$ or the setscrew connector element 170 during assembly of the stack 130 to electrically isolate the electrical connector element $132_1$–$132_3$ and the setscrew connector element 170 and to maintain the axial alignment and the length and diameter dimensions. Each electrical connector element $132_1$–$32_3$ and fluid seal $152_1$–$152_4$ has a predetermined axial length between annular ends thereof, and the stack length is defined by the combined axial lengths of the total number of electrical connector elements and fluid seals. Fluid seal $152_4$ is located at one end of the stack 130, and, in this case, a washer or spacer 104 is located at the other end of the stack 130.

Each electrical connector element 132 (i.e., $132_1$–$132_3$) is formed of a first part 134 and a second part 146 and a continuous coil spring 148 (each denoted in FIG. 12 by subscripts 1–4). The two parts 134 and 146 and the coil spring 148 are fitted together as depicted and the two parts 134 and 146 are attached together to form the electrical connector element 132. Again, the coil spring 48 is retained or trapped in the channel formed by the parts 134 and 146 and intrudes slightly into the connector element bore which becomes part of the stack bore 131, whereby the coil spring 148 is compressed by a lead connector element inserted into the stack bore 131. In this way, secure, frictional electrical and mechanical contact is made between lead connector elements $126_1$–$126_3$ and the header connector elements $132_1$–$132_3$.

An annular male flange 138 (each denoted in FIG. 12 by subscripts 1–4) of each electrical connector element 132 extends away from an annular end wall of the part 146 in parallel alignment with the connector element axis and the stack axis. A further annular male flange 136 (each denoted in FIG. 12 by subscripts 1–4) extends in the opposite direction away from the annular end wall of part 134 in parallel alignment with the connector element axis and the stack axis.

Each fluid seal 152 (i.e., $152_1$–$152_4$) is formed of a flexible elastomeric material, e.g. silicone rubber or a soft polyurethane or other polymer, and is generally tubular having a sidewall 154 extending between annular end walls defining a fluid seal lumen or bore 160 (each denoted in FIG. 12 by subscripts 1–4). Two more annular sealing rings 162 and 163 (each denoted in FIG. 12 by subscripts 1–4) are formed extending inward in the seal bore 160 so that the sealing rings 162, 163 intrude slightly into the stack bore 131, whereby the sealing rings 162, 163 are compressed by a lead insulator inserted into the connector bore defined by the stack bore 131. In this way, the sealing rings 162, 163 of the fluid seals $152_1$–$152_4$ seal against the insulation sleeves $128_1$–$128_4$ to seal the stack bore 131 and the electrical connections from fluid ingress.

As noted above, the stack 130 comprises a setscrew connector element 170 preferably located at one end of the stack 130. The setscrew connector element 170 comprises a setscrew connector block 175 and setscrew 172 fitted into a threaded bore 174. The connector block 175 is formed with a connector element bore 171 that is axially aligned with and part of the stack bore 131. The setscrew 172 and threaded bore 174 are transverse to the connector element bore 171. The connector element bore 171 is sized in diameter to receive the lead connector pin 129 and the setscrew 172 is adapted in this case to be tightened against it. The setscrew connector block 175 is formed with a single male flange 176 extending in parallel alignment with the stack bore 131 that is fitted into the annular female groove $158_1$ of the tubular fluid seal $152_1$.

As shown in FIG. 12, the tubular fluid seals $152_1$–$152_4$, the connector elements $132_1$–$132_3$, the reinforcing ring, and the setscrew connector element 170 are interlocked by fitting each respective annular male flange 136, 138, 176 into an annular female groove 156, 158 to assemble the stack 130. The spacer 104 is only employed to make the resulting stack 130 of a length that fits the length of a cavity or recess 119 in illustrated header base 114 and may be left out of the stack 130 when the cavity length and the stack length are otherwise within predetermined tolerances. The annular male flanges 136, 138, 106, 176, and annular female grooves 156, 158 are sized in width to provide an interference frictional fit. The annular flanges 136, 138, 106, 176 each fitted into an annular female groove 156, 158 stiffen the sidewalls 154 of each of the tubular fluid seals $152_1$–$152_4$ so that axially applied force during insertion or withdrawal of the lead connector assembly 122 into or out of the stack bore 131 does not unduly distort the fluid seals and sealing rings.

It should be noted that all of the fluid seals $152_1$–$152_4$ are identical having both annular female grooves 156 and 158 formed in the annular ends of the sidewall 154. In this case, the annular male flange 106 of an annular stiffening ring 102 is inserted into the annular groove $156_4$ of the fluid seal $152_4$ at the end of the stack 130. It should also be noted that the stiffening ring 102 and the annular male flanges 136, 138 are aligned in a plane with the sealing rings 162, 163 when inserted into the annular grooves 158 and 156, respectively. The annular male flange 106 of the stiffening ring 102 and the annular male flanges 106, 136, 138 reinforce the sealing rings 162, 163 in this embodiment. Again, it should be noted that sealing rings 162, 163 are not necessarily needed on all of the fluid seals $152_1$–$152_4$, but specifying sealing rings 162, 163 on all of the fluid seals $152_1$–$152_4$ simplifies parts specification and assembly of the stack 130.

Returning to FIG. 10, when the stack assembly is completed, the stack 130 is fitted into the cavity or recess 119 of the header base 114. One end of the cavity or recess 116 extends through the IPG header bore 117 and a seal 108 closes the other end of the recess. In IPG headers designed to have two header bores, two such stacks 130 and seals 108 are inserted side-by-side into respective side-by-side recesses 119 in the header base 114 that can be open to one another or separated. Electrical conductors, e.g., an array of preformed Niobium ribbons, are inserted into slots of the header base 114 and their free ends are welded to the connector elements of the stack 130. The exposed stack(s) 130 is over-molded with an elastomeric compound, e.g., silicone rubber or other polymers, to fill the remaining space of the recess or recesses 119 and present a finished outer surface. The annular flanges 136, 138, 106, 176 fitted into an annular female groove 156, 158 stiffen the sidewalls 154 of each of the tubular fluid seals $152_1$–$152_4$ so that externally applied pressure applied during sealing or molding of the stack 130 into the cavity or recess 119 or over-molding of the stack 130 with the header base 114. Optionally, a header cover formed of the same material as the header base 114 can then be fitted over and adhered to the over-molded assembly, e.g., by ultrasonic welding of the edges of the cover to the base 114. Or, the cover can be first fitted over the opening of the recess 119, and liquid polymer injected into the remaining space of the recess or recesses 119.

When the assembly is complete, the stack bore 131 is axially aligned with and effectively becomes the IPG header bore 117. The lead connector assembly 122 is inserted into the IPG header bore until the connector pin 129 is fully seated and extends through the setscrew connector bore 171, the bore of the spacer 104 and into a bore of the elastomeric seal 108. The setscrew 172 is tightened against that area of the connector pin 129 extending through bore 171 that it bears against.

While setscrew connector elements 70 and 170 are described as forming part of the stacks 30 and 130, it will be understood that the present invention can be practiced to form such stacks that do not include setscrew connector elements 70, 170 and that may either rely upon other forms of locking mechanisms known in the art or not employ a locking mechanism other than the frictional engagement of the stack components against the lead connector assembly. In this regard, one or more of the lead connector elements may include annular detent grooves into which the continuous coil springs expand to be fully seated and thereby increase the retention strength and the force required to pull the lead connector assembly partially or fully out of the IPG header bore.

While the male flanges 36, 38, 76, 78 and the female grooves 56, 58 as well as the male flanges 136, 138, 176 and the female grooves 156, 158 are depicted and described in these embodiments as "annular", it will be understood that they are intended to embrace equivalent structures that may not be annular or fully annular.

All patents and publications referenced herein are hereby incorporated by reference in their entireties.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described IMD embodiments and equivalents thereto, including monitors, now known and coming into existence during the term of the patent. Thus, it is expected that various changes, alterations, or modifications may be made to the invention as described herein without departing from the spirit and scope of the invention as defined by the appended claims.

What is claimed is:

1. In an IPG comprising an IPG housing containing electronic circuitry and an IPG connector header having a header bore for receiving and making connection between a lead connector assembly of an implantable medical lead comprising a plurality of lead connector elements arranged in-line and separated by lead insulator elements, an improved IPG connector header comprising:

a connector header base having an attachment surface shaped to be attached with a surface of the IPG housing, a header bore entrance into which the lead connector assembly is inserted to make the connection, and a cavity axially aligned with the header bore entrance;

a first plurality of electrically conductive, header connector elements each having a connector element bore sized to receive and make electrical contact with a lead connector element;

a second plurality of electrically insulating, flexible fluid seals each having a seal bore sized to receive a lead insulator element;

interlocking means disposed between each adjoining one of the first plurality of header connector elements and the second plurality of fluid seals for interlocking the first plurality of header connector elements with the second plurality of fluid seals in a stack of alternating header connector elements and fluid seals to electrically insulate the header connector elements from one another with the connector element bores in axial alignment with the fluid seal bores to define a stack bore and stack axis; and means for maintaining the stack within the connector header base with the stack bore axially aligned with the header bore entrance to define the header bore for receiving the lead connector assembly with header connector elements in electrical contact with the lead connector elements and fluid seals in contact with lead insulator elements, wherein the first plurality of header connector elements is formed of a sidewall extending between first and second end walls forming an interior channel, and further comprises a continuous coil spring fitted into and retained by the interior channel, whereby turns of the coil spring bear against lead connector elements inserted into the header connector element bore.

2. The IPG connector header of claim 1, wherein the interlocking means further comprises coupling means extending from each header connector element parallel to the stack axis and into the adjoining fluid seal to mechanically interlock the header connector elements and fluid seals.

3. The IPO connector header of claim 2, wherein the coupling means mechanically reinforces the fluid seals against forces tending to collapse or distort the fluid seals.

4. The IPG connector header of claim 1, wherein the seal bore of at least one of the second plurality of fluid seals is formed with a sealing ring that is sized to frictionally engage a lead insulator element inserted into the fluid seal bore.

5. In an IPG comprising an IPG housing containing electronic circuitry and an IPG connector header having a header bore for receiving and making connection between a lead connector assembly of an implantable medical lead comprising a plurality of lead connector elements arranged in-line and separated by lead insulator elements, an improved IPG connector header comprising:

a connector header base having an attachment surface shaped to be attached with a surface of the IPG housing, a header bore entrance into which the lead connector assembly is inserted to make the connection, and a cavity axially aligned with the header bore entrance;

a first plurality of electrically conductive, header connector elements each having a connector element bore sized to receive and make electrical contact with a lead connector element;

a second plurality of electrically insulating, flexible fluid seals each having a seal bore sized to receive a lead insulator element;

interlocking means disposed between each adjoining one of the first plurality of header connector elements and the second plurality of fluid seals for interlocking the first plurality of header connector elements with the second plurality of fluid seals in a stack of alternating header connector elements and fluid seals to electrically insulate the header connector elements from one another with the connector element bores in axial alignment with the fluid seal bores to define a stack bore and stack axis;

means for maintaining the stack within the connector header base with the stack bore axially aligned with the header bore entrance to define the header bore for receiving the lead connector assembly with header connector elements in electrical contact with the lead connector elements and fluid seals in contact with lead insulator elements; and a setscrew connector element supporting a setscrew aligned radially with a connector block bore, and further interlocking means disposed between the setscrew connector element and at least one of the second plurality of fluid seals for interlocking the setscrew connector element into the stack with the connector block bore in axial alignment with the fluid seal bores and the connector element bores to define the stack bore and stack axis.

6. The IPG connector header of claim 5, wherein the further interlocking means further comprises coupling means extending from the setscrew connector element parallel to the stack axis and into the adjoining fluid seal to mechanically interlock the setscrew connector element with the header connector elements and fluid seals.

7. The IPG connector header of claim 6, wherein the further coupling means mechanically reinforces the fluid seals against forces tending to collapse or distort the fluid seals.

8. The IPG connector header of claim 5, wherein the connector block bore is dimensioned to receive a lead connector element when the lead connector assembly is inserted into the header, and the setscrew is adapted to be tightened against the lead connector element.

9. In an IPG comprising an IPG housing containing electronic circuitry and an IPG connector header having a header bore for receiving and making connection between a lead connector assembly of an implantable medical lead comprising a plurality of lead connector elements arranged in-line and separated by lead insulator elements, an improved IPG connector header comprising:
 a connector header base having an attachment surface shaped to be attached with a surface of the IPG housing, a header bore entrance into which the lead connector assembly is inserted to make the connection, and a cavity axially aligned with the header bore entrance;
 a first plurality of electrically conductive, header connector elements each having a connector element bore sized to receive and make electrical contact with a lead connector element;
 a second plurality of electrically insulating, flexible fluid seals each having a seal bore sized receive a lead insulator element;
 interlocking means disposed between each adjoining one of the first plurality of header connector elements and the second plurality of fluid seals for interlocking the first plurality of header connector elements with the second plurality of fluid seals in a stack of alternating header connector elements and fluid seals to electrically insulate the header connector elements from one another with the connector element bores in axial alignment with the fluid seal bores to define a stack bore and stack axis; and
 means for maintaining the stack within the connector header base with the stack bore axially aligned with the header bore entrance to define the header bore for receiving the lead connector assembly with header connector elements in electrical contact with the lead connector elements and fluid seals in contact with lead insulator elements, wherein the second plurality of fluid seals exceeds the first plurality of electrical connector elements whereby end fluid seals are fixed at each end of the stack by the interlocking means, and further comprising reinforcing means fitted to the end fluid seals to mechanically reinforce the fluid seals against forces tending to collapse or distort the fluid seals.

10. In an IPG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising:
 a connector header base having an attachment surface shaped to be attached with a surface of the IPG housing, a header bore entrance into which the lead connector assembly is inserted to make the connection, and a cavity axially aligned with the header bore entrance;
 a first plurality of electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;
 a second plurality of electrically insulating, flexible fluid seals each having a seal bore sized to receive a lead insulator element, each fluid seal formed of a sidewall extending between first and second end walls and having a first female groove formed into the first end wall and a second female groove formed into a second end wall;
 wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore; and
 means for maintaining the stack within the connector header base with the stack bore axially aligned with the header bore entrance to define the header bore for receiving the lead connector assembly with header connector elements in electrical contact with the lead connector elements and fluid seals in contact with lead insulator elements.

11. In an IPG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising:
 a connector header base having an attachment surface shaped to be attached with a surface of the IPG housing, a header bore entrance into which the lead connector assembly is inserted to make the connection, and a cavity axially aligned with the header bore entrance;
 a first plurality of electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;
 a second plurality of electrically insulating, flexible fluid seals each having a seal bore sized to receive a lead insulator element, each fluid seal formed of a sidewall extending between first and second end walls and having a first female groove formed into the first end wall and a second female groove formed into a second end wall;

wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore; and means for maintaining the stack within the connector header base with the stack bore axially aligned with the header bore entrance to define the header bore for receiving the lead connector assembly with header connector elements in electrical contact with the lead connector elements and fluid seals in contact with lead insulator elements, wherein the interlocking grooves and flanges are annular and are formed to extend parallel to the stack axis to mechanically interlock the header connector elements and fluid seals.

12. In an IPG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising:

a connector header base having an attachment surface shaped to be attached with a surface of the IPG housing, a header bore entrance into which the lead connector assembly is inserted to make the connection, and a cavity axially aligned with the header bore entrance;

a first plurality of electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;

a second plurality of electrically insulating; flexible fluid seals each having a seal bore sized to receive a lead insulator element, each fluid seal formed of a sidewall extending between first and second end walls and having a first female groove formed into the first end wall and a second female groove formed into a second end wall;

wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore; and means for maintaining the stack within the connector header base with the stack bore axially aligned with the header bore entrance to define the header bore for receiving the lead connector assembly with header connector elements in electrical contact with the lead connector elements and fluid seals in contact with lead insulator elements, wherein the interlocking grooves and flanges are annular and are formed to extend parallel to the stack axis to mechanically reinforce the fluid seals against forces tending to collapse or distort the fluid seals.

13. In an IPG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising:

a connector header base having an attachment surface shaped to be attached with a surface of the IPG housing, a header bore entrance into which the lead connector assembly is inserted to make the connection, and a cavity axially aligned with the header bore entrance;

a first plurality of electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;

a second plurality of electrically insulating, flexible fluid seals each having a seal bore sized to receive a lead insulator element, each fluid seal formed of a sidewall extending between first and second end walls and having a first female groove formed into the first end wall and a second female groove formed into a second end wall;

wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore; and means for maintaining the stack within the connector header base with the stack bore axially aligned with the header bore entrance to define the header bore for receiving the lead connector assembly with header connector elements in electrical contact with the lead connector elements and fluid seals in contact with lead insulator elements, wherein the first plurality of header connector elements is formed of a sidewall extending between first and second end walls forming an interior channel, and further comprises a continuous coil spring fitted into and retained by the interior channel, whereby turns of the coil spring bear against lead connector elements inserted into the header connector element bore.

14. In an PG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising:

a connector header base having an attachment surface shaped to be attached with a surface of the IPG housing, a header bore entrance into which the lead connector assembly is inserted to make the connection, and a cavity axially aligned with the header bore entrance;

a first plurality of electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;

a second plurality of electrically insulating, flexible fluid seals each having a seal bore sized to receive a lead insulator element, each fluid seal formed of a sidewall extending between first and second end walls and having a first female groove formed into the first end wall and a second female groove formed into a second end wall;

wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore; and means for maintaining the stack within the connector header base with the stack bore axially aligned with the header bore entrance to define the header bore for receiving the lead connector assembly with header connector elements in electrical contact with the lead connector elements and fluid seals in contact with lead insulator elements, wherein the seal bore of at least one of the second plurality of fluid seals is formed with a sealing ring that is sized to frictionally engage a lead insulator element inserted into the fluid seal bore.

15. In an IPG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising:

a connector header base having an attachment surface shaped to be attached with a surface of the IPG housing, a header bore entrance into which the lead connector assembly is inserted to make the connection, and a cavity axially aligned with the header bore entrance;

a first plurality electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;

a second plurality of electrically insulating, flexible fluid seals each having a seal bore sized to receive a lead insulator element, each fluid seal formed of a sidewall extending between first and second end walls and having a first female groove formed into the first end wall and a second female groove formed into a second end wall;

wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore;

means for maintaining the stack within the connector header base with the stack bore axially aligned with the header bore entrance to define the header bore for receiving the lead connector assembly with header connector elements in electrical contact with the lead connector elements and fluid seals in contact with lead insulator elements; and a setscrew connector element supporting a setscrew aligned radially with a connector block bore and formed with a flange extending from the setscrew connector element into a mating groove of at least one of the second plurality of fluid seals for interlocking the setscrew connector element into the stack with the connector block bore in axial alignment with the fluid seal bores and the connector element bores to define the stack bore and stack axis.

16. The IPG connector header of claim 15, wherein the connector block bore is dimensioned to receive a lead connector element when the lead connector assembly is inserted into the header, and the setscrew is adapted to be tightened against the lead connector element.

17. In an IPG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising:

a connector header base having an attachment surface shaped to be attached with a surface of the IPG housing, a header bore entrance into which the lead connector assembly is inserted to make the connection, and a cavity axially aligned with the header bore entrance;

a first plurality of electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;

a second plurality of electrically insulating, flexible fluid seals each having a seal bore sized to receive a lead insulator element, each fluid seal formed of a sidewall extending between first and second end walls and having a first female groove formed into the first wall and a second female groove formed in to a second end wall;

wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore;

means for maintaining the stack within the connector header base with the stack bore axially aligned with the header bore entrance to define the header bore for receiving the lead connector assembly with header connector elements in electrical contact with the lead connector elements and fluid seals in contact with lead insulator elements; and a setscrew connector element supporting a setscrew aligned radially with a connector block bore and formed with a first flange extending from a first side of the setscrew connector element into a mating groove of a first one of the second plurality of fluid seals and with a second flange extending from a second side of the setscrew connector element into a mating groove of a second one of the second plurality of fluid seal for interlocking the setscrew connector element into the stack with the connector block bore in axial alignment with the fluid seal bores and the connector element bores to define the stack bore and stack axis.

18. The IPG connector header of claim 17, wherein the connector block bore is dimensioned to receive a lead connector element when the lead connector assembly is inserted into the header, and the setscrew is adapted to be tightened against the lead connector element.

19. In an IPG comprising an IPG housing and an IPG connector header having a header bore for receiving and making connection between a lead connector assembly of an implantable medical lead comprising a plurality of lead connector elements arranged in-line and separated by lead insulator elements, an improved IPG connector header comprising;

a connector header base having attachment surface shaped to be attached with a surface of the IPG housing, a header bore entrance into which the lead connector assembly is inserted to make the connection, and a cavity axially aligned with the header bore entrance;

a first plurality of electrically conductive, header connector elements each having a connector element bore sized to receive and make electrical contact with a lead connector element, each header connector element formed of a sidewall extending between first and second end walls and having a first male flange extending away from the first end wall and a second connector annular male flange extending away from the second end wall;

a second plurality of electrically insulating, flexible fluid seals each having a seal bore sized to receive a lead insulator element, each fluid seal formed of a sidewall extending between first and second end walls and having a first female groove formed into the first end wall and a second female groove formed into a second end wall;

wherein predetermined ones of the first and second flanges of the first plurality of header connector elements are inserted into the first and second grooves of the second plurality of fluid seals to interlock the first plurality of header connector elements with the second plurality of fluid seals in a stack with the connector element bores in axial alignment with the fluid seal bores to define a stack axis and stack bore; and means for maintaining the stack within the connector header base with the stack bore axially aligned with the header bore entrance to define the header bore for receiving the lead connector assembly with header connector elements in electrical contact with the lead connector elements and fluid seals in contact with lead insulator elements, wherein the second plurality of fluid seals exceeds the first plurality of electrical connector elements whereby end fluid seals are fixed at each end of the stack by the interlocking flanges and grooves exhibiting empty end grooves in each end fluid seal, and further comprising a reinforcing flange fitted to end grooves of the end fluid seals to mechanically reinforce the fluid seals against forces tending to collapse or distort the fluid seals.

* * * * *